United States Patent [19]
Simon et al.

[11] Patent Number: 5,066,478
[45] Date of Patent: Nov. 19, 1991

[54] RADIO LABELED ORGANIC AMINE PHOSPHONIC ACID COMPLEXES FOR THE TREATMENT OF CALCIFIC TUMORS

[75] Inventors: Jaime Simon, Angleton; David A. Wilson, Richwood, both of Tex.; Wynn A. Volkert; David E. Troutner, both of Columbia, Mo.; William F. Goeckeler, Midland, Mich.

[73] Assignee: The Dow Chemical Company, Midland, Mich.

[21] Appl. No.: 472,506

[22] Filed: Jan. 30, 1990

Related U.S. Application Data

[62] Division of Ser. No. 50,263, May 14, 1987, Pat. No. 4,898,724.

[51] Int. Cl.$^5$ .............................................. A61K 43/00
[52] U.S. Cl. ................................... 424/1.1; 534/10
[58] Field of Search ....................... 424/1.1; 534/14, 10

[56] References Cited

U.S. PATENT DOCUMENTS

| | | | |
|---|---|---|---|
| 3,851,044 | 9/1972 | Adler et al. | 423/249 |
| 3,852,414 | 12/1974 | Adler et al. | 424/1 |
| 3,931,396 | 1/1976 | Bardy et al. | 424/1 |
| 3,965,254 | 6/1976 | Tate et al. | 424/1 |
| 3,989,730 | 11/1976 | Subramanian et al. | 260/429.7 |
| 4,017,596 | 4/1977 | Loberg et al. | 424/1 |
| 4,075,314 | 2/1978 | Wolfangel et al. | 424/1 |
| 4,104,366 | 8/1978 | Schmidt Dunker et al. | 424/1 |
| 4,399,817 | 8/1983 | Benedict | 406/20 |
| 4,504,463 | 3/1985 | Van Duzee | 424/1 |
| 4,508,704 | 4/1985 | Simon et al. | 424/1 |
| 4,515,767 | 5/1985 | Simon et al. | 424/1 |
| 4,560,548 | 12/1985 | Simon et al. | 424/1 |
| 4,606,907 | 8/1988 | Simon et al. | 424/1.1 |
| 4,752,464 | 6/1988 | Lieberman et al. | 424/1 |
| 4,897,254 | 1/1990 | Simon et al. | 424/1.1 |

FOREIGN PATENT DOCUMENTS 210043A 1/1987 European Pat. Off. .

OTHER PUBLICATIONS

J. Nucl. Med. 1, pp. 1–13 (1960).
J. Nucl. Med. 10, pp. 49–51 (1969).
Seminar of Nucl. Med. IX, (2), pp. 114–120 (1979).
J. Nucl. Med. 24, P-125 (1983).
J. Nucl. Med. 25, pp. 1356–1361 (1984).
J. Nucl. Med. 25, P-126 (1984).
Int. J. App. Rad. & Isotopes 14, pp. 129–135 (1963).
6th Intl. Symposium on Rad. Pharmacology #140.
6th Intl. Symposium on Rad. Pharmacology #141.
Chem. Abstracts 96:14590m.
Chem. Abstracts 106:67404k.
Chem. Abstracts 107:111815s.
Chem. Abstracts 107:111887s.

*Primary Examiner*—John S. Maples
*Attorney, Agent, or Firm*—Karen L. Kimble

[57] ABSTRACT

Particle-emitting radionuclides, e.g. Gd-159, Ho-166, Lu-177 and Yb-175, have been complexed with organic aminoalkylenephosphonic acids wherein the nitrogen and phosphorus are interconnected by an alkylene group or substituted alkylene group. These complexes have been found useful in compositions for the therapeutic treatment of calcific tumors in animals and in relief of bone pain.

87 Claims, No Drawings

RADIO LABELED ORGANIC AMINE PHOSPHONIC ACID COMPLEXES FOR THE TREATMENT OF CALCIFIC TUMORS

CROSS-REFERENCE TO RELATED APPLICATION

This is a divisional of application Ser. No. 050,263, filed May 14, 1987, now U.S. Pat. No. 4,898,724.

This application is a continuation-in-part of our co-pending application Ser. No. 803,376 filed Dec. 4, 1985, now abandoned, which is a continuation-in-part of Ser. No. 738,010 filed May 28, 1985, now abandoned, which is a continuation-in-part of Ser. No. 616,985, filed June 4, 1984, now abandoned.

BACKGROUND OF THE INVENTION

The development of bone metastases is a common and often catastrophic event for a cancer patient. The pain, pathological fractures, frequent neurological deficits and forced immobility caused by these metastatic lesions significantly decrease the quality of life for the cancer patient. The number of patients that contract metastatic disease is large since nearly 50% of all patients who contract breast, lung or prostate carcinoma will eventually develop bone metastases. Bone metastases are also seen in patients with carcinoma of the kidney, thyroid, bladder, cervix and other tumors, but collectively, these represent less than 20% of patients who develop bone metastases. Metastatic bone cancer is rarely life threatening and occasionally patients live for years following the discovery of the bone lesions. Initially, treatment goals center on relieving pain, thus reducing requirements for narcotic medication and increasing ambulation. Clearly, it is hoped that some of the cancers can be cured.

The use of radionuclides for treatment of cancer metastatic to the bone dates back to the early 1950's. It has been proposed to inject a radioactive particle-emitting nuclide in a suitable form for the treatment of calcific lesions. It is desirable that such nuclides be concentrated in the area of the bone lesion with minimal amounts reaching the soft tissue and normal bone. Radioactive phosphorus (P-32 and P-33) compounds have been proposed, but the nuclear and biolocalization properties limit the use of these compounds. (Kaplan, E., et al, *Journal of Nuclear Medicine*, Vol. 1, No. 1, page 1, 1960): (U.S. Pat. No. 3,965,254).

Another attempt to treat bone cancer has been made using phosphorus compounds containing a boron residue. The compounds were injected into the body (intravenously) and accumulated in the skeletal system. The treatment area was then irradiated with neutrons in order to activate the boron and give a therapeutic radiation dose. (U.S. Pat. No. 4,399,817).

In the above mentioned procedures, it is not possible to give therapeutic doses to the tumor without substantial damage to normal tissues. In many cases, especially for metastatic bone lesions, the tumor has spread throughout the skeletal system and amputation or external beam irradiation is not practical. (*Seminars in Nuclear Medicine*, Vol. IX, No. 2, April, 1979).

The use of Re-186 complexed with a diphosphonate has also been proposed. (Mathieu, L. et al, *Int. J. Applied Rad. & Isotopes*, Vol. 30, pp. 725–727, 1979: Weinenger, J., Ketring, A. R., et al, *Journal of Nuclear Medicine*, Vol. 24, No. 5, P125, 1983). However, the preparation and purification needed for this complex limits its utility and wide application.

Strontium-89 has also been proposed for patients with metastatic bone lesions. However, the long half-life (50.4 days), high blood levels and low lesion to normal bone ratios limit the utility. (Firusian, N., Mellin, P., Schmidt, C. G., *The Journal of Urology*, Vol. 116, page 764, 1976; Schmidt, C. G., Firusian, N., *Int. J. Clin. Pharmacol.*, 93:199–205, 1974).

A palliative treatment of bone metastases has been reported which employed I-131 labelled α-amino-(3-iodo-4-hydroxybenzylidene)diphosphonate (Eisenhut, M, *Journal of Nuclear Medicine*, Vol. 25, No. 12, pp. 1356—1361, 1984). The use of radioiodine as a therapeutic radionuclide is less than desirable due to the well known tendency of iodine to localize in the thyroid. Eisenhut lists iodide as one of the possible metabolites of this compound.

SUMMARY OF THE INVENTION

Certain particle-emitting radionuclides, e.g. Samarium-153, have been complexed with certain organic aminoalkylenephosphonic acids, i.e. aminophosphonic acids in which the nitrogen and phosphorus atoms are interconnected by an alkylene or substituted alkylene group, for example ethylenediaminetetramethylenephosphonic acid, and physiologically acceptable salts thereof. Certain compositions containing these complexes have been found useful for therapy of calcific tumors in animals. The administration of the therapeutic compositions has been palliative to the animal, for example by alleviating pain and/or inhibiting tumor growth and/or causing regression of tumors and/or destroying the tumors.

As used herein, the term "animals" includes humans: the term "calcific tumors" includes primary tumors, where the skeletal system is the first site of involvement, invasive tumors where the primary tumor invades the skeletal system or other tissue tumors which calcify, and metastatic bone cancer where the neoplasm spreads from other primary sites, e.g. prostate and breast, into the skeletal system.

DETAILED DESCRIPTION OF THE INVENTION

The compositions of this invention are used for the therapeutic treatment of calcific tumors in animals. These compositions contain certain radionuclides complexed with certain aminophosphonic acids, or physiologically acceptable salts thereof. As will be more fully discussed later, the properties of the radionuclide, of the aminophosphonic acid and of the complex formed therefrom are important considerations in determining the effectiveness of any particular composition employed for such treatment.

Particle-emitting radionuclides employed in the compositions of the invention are capable of delivering a high enough localized ionization density to alleviate pain and/or inhibit tumor growth and/or cause regression of tumors, and/or destroy the tumor and are capable of forming complexes with the aminophosphonate ligands described herein. The radionuclides found to be useful in the practice of the invention are Samarium-153 (Sm-153), Holmium-166 (Ho-166), Ytterbium-175 (Yb-175), Lutetium-177 (Lu-177), and Gadolinium-159 (Gd-159).

The organic aminophosphonic acids which have been found useful in the compositions of this invention are organic amine or substituted organic amine compounds wherein the amine nitrogen and the phosphorus of the phosphonic acid moiety are interconnected by an alkylene or substituted alkylene group having the formula

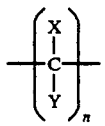

wherein X and Y are independently selected from hydrogen, hydroxyl, carboxyl, phosphonic, and hydrocarbon radicals having from 1-8 carbon atoms and physiologically acceptable salts of the acid radicals and n is 1-3 with the proviso that when n>1 each X and Y may be the same as or different from the X and Y of any other carbon atom.

The following structural formulas represent some of the ligands which can be used in the compositions of this invention:

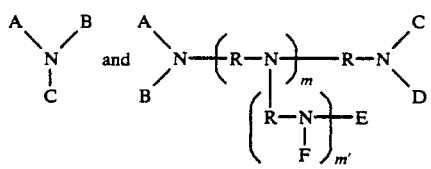

wherein substituents A, B, C, D, E and F are independently selected from hydrogen,

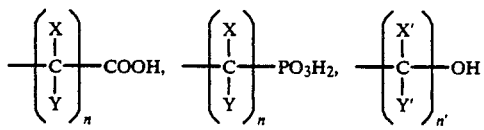

and physiologically acceptable salts of the acid radicals wherein X, Y, and n are as previously defined, X' and Y' are independently hydrogen, methyl or ethyl radicals, n' is 2 or 3 and m and m' each is independently 0-10, with the proviso that at least one of said nitrogen substituents is a phosphorus-containing group as previously defined herein, and wherein R is a hydrocarbon residue which can be a linear, branched, cyclic, heterocyclic, substituted heterocyclic, or a fused ring-type structure: with the further proviso that when m or m'<1 the E and F substituents may be the same as or different from any other substituent of any other nitrogen atom and each R can be the same as or different from any other R. In addition, cyclic amines containing the above mentioned substituents, provided that at least one is a phosphorous-containing group as previously defined, are useful in the compositions of the invention.

Some specific, but non-limiting, examples of ligands which are included by the above structures are ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), tris(2-aminoethyl)aminehexamethylenephosphonic acid (TTHMP), 1-carboxyethylenediaminetetramethylenephosphonic acid (CEDTMP) and bis(aminoethylpiperazine)tetramethylenephosphonic acid (AEPTMP).

For the purpose of the present invention, the complexes described herein and physiologically acceptable salts thereof are considered equivalent in the therapeutically effective compositions. Physiologically acceptable salts refer to the acid addition salts of those bases which will form a salt with at least one acid group of the ligand or ligands employed and which will not cause a significant adverse physiological effect when administered to an animal at dosages consistent with good pharmacological practice. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Physiologically acceptable salts may be prepared by treating the acid with an appropriate base.

Complexes employed in the compositions of the present invention must fit certain criteria insofar as possible. It should be recognized that there are many ligands, or complexing agents, which are included by our definition of the aminophosphonic acids in which the nitrogen of the amine and the phosphorus of the phosphonic acid group are interconnected by an alkylene group. Many may also contain other functional groups as substituents for some, but not all, of the amine hydrogens of the ligand. It should also be recognized that the properties of the particular radionuclide are important. The disadvantage of any one property may be overcome by the superiority of one or more of the properties of either ligand or radionuclide and their combination as the complex must be considered in toto.

The following is a discussion of the criteria which must be considered in choosing any particular therapeutically effective combination of radionuclide and ligand. Certain combinations, due to one or more undesirable properties, may not be therapeutically useful or effective, e.g. too much radioactivity localizing in non-osseous tissue.

The radionuclide must be delivered preferentially to the bone rather than to soft tissue. Most particularly, uptake in either liver or bone marrow is undesirable. Another important criterion is the ratio of the amount of radionuclide taken up by the cancerous bone to that by normal bone. High ratios are preferred. Also, the radionuclide should be cleared rapidly from non-osseous tissue to avoid unnecessary damage to such tissues, e.g., it should clear rapidly from the blood.

For the purpose of convenience the abbreviations given hereinbefore will be used hereinafter to denote the respective radionuclides and aminophosphonic acids.

Preferred embodiments of the present invention are therapeutically effective or useful compositions containing complexes of at least one radionuclide selected from Gd-159, Ho-166, Lu-177, Sm-153 and Yb-175 with at least one ligand selected from EDTMP, DTPMP, HEEDTMP, NTMP, TTHMP, CEDTMP and AEPTMP, or a physiologically acceptable salt(s) thereof.

Not all compositions containing radionuclides and ligands are therapeutically useful. Thus, for example, a composition containing Sm-153 and monoethanolaminedimethylenephosphonic acid was unacceptable because a significant portion of the radioactivity localized in the liver.

Combinations of the various above noted radionuclides can be administered for the therapeutic treatment of calcific tumors. The combinations can be complexed as herein described by complexing them simultaneously, mixing two separately complexed radionuclides, or administering two different complexed radionuclides sequentially. It may be possible to achieve the same beneficial results of high delivery of the radionuclide to the area of the tumor, but with little soft tissue damage, by administering the ligand and the radionuclide in a manner which allows formation of the radionuclide-chelant complex in situ such as by simultaneous or near simultaneous administration of the radionuclide and an appropriate amount of ligand or by the administration of ligand and a radionuclide complexed with a weaker ligand, i.e., one which undergoes ligand exchange with the ligands of this invention, such that the desired radionuclide-chelant complex is formed via ligand exchange in situ. The composition may be administered as a single dose or as multiple doses over a longer period of time.

The aminophosphonic acids can be prepared by a number of known synthetic techniques. Of particular importance is the reaction of a compound containing at least one reactive amine hydrogen with a carbonyl compound (aldehyde or ketone) and phosphorous acid or derivative thereof.

Amine precursors employed in making the aminophosphonic acids employed in the present invention are commercially available products or may be prepared readily by methods known to those skilled in the art of organic synthesis.

Methods for carboxyalkylating to obtain the amine derivatives containing one or more carboxyalkyl groups are well known (U.S. Pat. No. 3,726,912) as are the methods which give alkyl phosphonic and hydroxyalkyl (U.S. Pat. No. 3,398,198) substituents on the amine nitrogens.

Radionuclides can be produced in several ways. In a nuclear reactor, a nuclide is bombarded with neutrons to obtain a radionuclide, e.g.

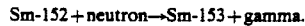

Sm-152+neutron→Sm-153+gamma.

Another method of obtaining radionuclides is by bombarding nuclides with linear accelerator or cyclotron-produced particles. Yet another way of obtaining radionuclides is to isolate them from fission product mixtures. The method of obtaining the radionuclide is not critical to the present invention.

To irradiate $Sm_2O_3$ for production of Sm-153, the desired amount of target was first weighed into a quartz vial, the vial was flame sealed under vacuum and welded into an aluminum can. The can was irradiated for the desired length of time, cooled for several hours and opened remotely in a hot cell. The quartz vial was removed and transferred to a glove box, crushed into a glass vial which was then sealed with a rubber septum and an aluminum crimp cap. One milliliter of 1–4 M HCl was then added to the vial via syringe to dissolve the $Sm_2O_3$. Once dissolved, the solution was diluted to the appropriate volume by addition of water. The solution was removed from the original dissolution vial which contains chards of the crushed quartz vial and transferred via syringe to a clean glass serum vial. This solution was then used for complex preparation. Similar procedures were used to prepare Lu-177, Yb-175, Gd-159, and Ho-166.

When aqueous solutions of metal ions are mixed with solutions containing complexing agents, such as those described in this invention, a complex between the metal ion and the ligand can be formed as shown by the equation below.

$$M + L \rightleftharpoons M \cdot L$$

The reaction is believed to be an equilibrium such that the concentrations of metal (M) and complexing agent, or ligand (L), can affect the concentration of species present in solution. Competing side reactions, such as metal hydroxide formation, can also occur in aqueous solution, thus

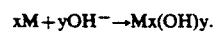

$$xM + yOH^- \rightarrow M_x(OH)_y.$$

The $OH^-$ concentration in solution, which is related to pH is, therefore, an important parameter to be considered. If the pH is too high, the metal tends to form metal hydroxides rather than complexes. The complexing agents may also be adversely affected by low pH. Complexation may require the loss of proton(s); therefore at low pH, conditions may not be favorable for complexation to occur. Consideration must be given to the solubility characteristics of the ligand, radionuclide, and complex. Although not limited thereto, a pH in the range of from 5 to 11 is preferred for complexation.

The metal and ligand may be combined under any conditions which allow the two to form a complex. Generally, mixing in water at a controlled pH (the choice of pH is dependent upon the choice of ligand and metal) is all that is required.

The ratio of ligand to metal is a result of two competing considerations. As indicated above, the ligand and metal are believed to be in equilibrium with the complex. As appreciated by one skilled in the art of radiochemistry, only a portion of the metal which is irradiated will become radioactive. In the practice of the invention it is preferred that an amount of the ligand be employed that is sufficient to insure that all of the radionuclide present is complexed since any uncomplexed radionuclide may localize in soft tissue. To insure complexation of the radionuclide it is preferred that the amount of ligand used be in excess of the total amount of metal present, i.e. radioactive metal plus non-radioactive metal plus any other metals present that can complex with the ligand. Thus, in the practice of the invention it is desirable to employ the complexed nuclide in the presence of an excess of ligand. Such excess should provide an amount sufficient to inhibit significant uptake of the radionuclide by soft tissue. The excess ligand may be the same as or different from that used to complex the radionuclide. However, too much free ligand may have adverse effects, e.g. it may be toxic to the patient or result in less favorable biolocalization of the radionuclide.

Most of the complexes employed in this invention were prepared as follows: the desired amount of ligand was placed in a vial and dissolved by addition of water. At some higher ligand concentrations, it was necessary to add base in order to completely dissolve the ligand. Heating was also found to be useful for dissolving the ligands. The appropriate amount of the samarium or other radionuclides in the stock solution described above was then added to the ligand solution. The pH of the resulting solution was then raised to the appropriate level (usually 7-8) by addition of NaOH.

The invention described herein provides a means of delivering a therapeutic amount of radioactivity to calcific tumors. However, it may also be desirable to administer a "sub-therapeutic" amount to determine the fate of the radionuclide using a scintillation camera prior to administering a therapeutic dose. Therapeutic doses will be administered in sufficient amounts to alleviate pain and/or inhibit tumor growth and/or cause regression of tumors and/or kill the tumor. Amounts of radionuclide needed to provide the desired therapeutic dose will be determined experimentally and optimized for each particular composition. The amount of radioactivity required to deliver a therapeutic dose will vary with the individual composition employed. The composition to be administered may be given in a single treatment or fractionated into several portions and administered at different times. Administering the composition in fractionated doses may make it possible to minimize damage to non-target tissue. Such multiple dose administration may be more effective.

The compositions of the present invention may be used in conjunction with other active agents and/or ingredients that enhance the therapeutic effectiveness of the compositions and/or facilitate easier administration of the compositions.

Studies to determine the qualitative biodistribution of the various radionuclides were conducted by injecting the compositions into rats and obtaining the gamma ray images of the entire animal at various times up to two hours after injection.

Quantitative biodistributions were obtained by injecting 50-100 microliters of the composition into the tail vein of unanesthetized male Sprague Dawley rats. The rats were then placed in cages lined with absorbent paper in order to collect all urine excreted prior to sacrifice. After a given period of time, the rats were sacrificed by cervical dislocation and the various tissues dissected. The samples were then rinsed with saline, blotted dry on absorbent paper and weighed. The radioactivity in the samples was measured with a NaI scintillation counter.

Biolocalization studies were also performed in rabbits. The rabbits were injected with 100-250 microliters of the composition into the marginal ear vein. In studies where blood clearance was measured, blood samples were taken through a heparinized cannula placed in the marginal vein of the ear not used for injection. Three hours after injection, a blood sample was taken from each rabbit by cardiac puncture and each animal was sacrificed by injection of a commercial euthanasia solution. After sacrifice, images were obtained by placing the carcass directly on the face of a large field-of-view scintillation camera.

Uptake of the radionuclide in the lesion compared to uptake in normal bone, or lesion/normal bone ratios, is a particularly important parameter for determining the suitability of any composition for therapy. To determine the lesion to normal bone ratios, a modified drill hole method (Subramanian, G. et al., 19th Intl. Annual Meetings of S.N.M., Bern, Switzerland, September 8-11, 1981) was used. Thus, two holes were drilled into the surface of the tibia of a rabbit in order to damage the bone. Seven to ten days later, the animal was injected with the radionuclide composition. After three hours, the rabbit was anesthetized and imaged using an Anger camera and pinhole collimator.

The following examples show representative preparations of aminophosphonic acid ligands and complexes of the ligands with the radionuclides and the use of these compositions.

EXAMPLE 1

Into a suitable reaction vessel equipped with a thermometer, magnetic stirring bar, dropping funnel, and an atmosphere of nitrogen were charged phosphorous acid (94.5 g) and degassed water (100 ml). Dissolution of the phosphorous acid was achieved by stirring and then concentrated hydrochloric acid (112 ml) was added. The dropping funnel was charged with ethylenediamine (15 g) and adjusted to allow dropwise addition of the amine to the acidic solution. When addition was complete a heating mantle was installed and the solution refluxed for one hour. At the end of this time the dropping funnel was charged with formaldehyde (85 g of a 37% aqueous solution) which was added dropwise over a two hour period with continued heating to maintain reflux during the addition. After all the formaldehyde was added, the reaction mixture was stirred under reflux for an additional two hours, then allowed to cool slowly overnight during which time the product precipitated. Vacuum filtration followed by cold water washing yielded ethylenediaminetetramethylenephosphonic acid (EDTMP).

EXAMPLE 2

A quantity of 25 to 35 milligrams of EDTMP was weighed into a vial and dissolved using 0.75 ml of distilled water. To this, 0.25 ml of Sm-153 ($\sim$10 mCi) in dilute HCl was added. The pH of the resulting solution was then adjusted to 10 by addition of NaOH. The resulting solution was heated to between 60°-70° C. for 30 minutes in a water bath. The pH of the solution was then adjusted to 7-8 by addition of HCl.

Laboratory rats were injected with the above complex (50-100 $\mu$l) via the tail vein. After 2 hours, the animals were sacrificed by cervical dislocation and organs and tissues removed. Samples were counted with a NaI counter to determine the biolocalization of the radionuclide. It was found that a significant amount (55-65 percent) of the radioactivity was concentrated in the skeletal system with very little soft tissue uptake. Most of the radioactivity not found in the skeleton was cleared through the kidneys into the urine. Sointillation scans of animals treated in the same manner showed the radioactivity concentrating in the skeletal system. The lesion to normal bone ratio was approximately equal to that of Tc-99m-MDP (MDP refers to methylene diphosphonate), a commercially available diagnostic bone agent.

EXAMPLE 3

Into a suitable reaction vessel equipped with a thermometer, magnetic stirring bar, dropping funnel, and an atmosphere of nitrogen were charged phosphorous acid (94.5g) and degassed water (100 ml). Dissolution of the phosphorous acid was achieved by stirring and concentrated hydrochloric acid (112 ml) was added. The dropping funnel was charged with diethylenetriamine (20.6 g) and adjusted to allow dropwise addition of the amine to the acidic solution. When addition was complete a heating mantle was installed and the solution refluxed for one hour. At the end of this time the dropping funnel was charged with formaldehyde (85 g of a 37% aqueous solution) which was added dropwise over a two hour period with continued heating to maintain reflux during the addition. After all the formaldehyde was added, the reaction mixture was stirred under reflux for an additional two hours, then allowed to cool. Diethylenetriaminepentamethylenephosphonic acid (DTPMP) was isolated from the reaction mixture.

EXAMPLE 4

A quantity of 20 to 30 milligrams of DTPMP was weighed into a vial and dissolved using 0.75 ml of distilled water. To this, 0.25 ml of Sm-153 (~10 mCi) in dilute HCl was added. The pH of the resulting solution was then adjusted to 10 by addition of NaOH. The solution was then heated to between 60°-70° C. for 30 minutes in a water bath. The pH of the solution was then adjusted to 7-8 by addition of HCl. This composition was then injected into rats and the biolocalization of Sm-153 was determined.

EXAMPLE 5

Into a suitable reaction vessel equipped with a thermometer, magnetic stirring bar, dropping funnel, and an atmosphere of nitrogen were charged phosphorous acid (94.5 g) and degassed water (100 ml). Dissolution of the phosphorous acid was achieved by stirring and concentrated hydrochloric acid (112 ml) was added. The dropping funnel was charged with N-hydroxyethylethylenediamine (34.6 g) and adjusted to allow dropwise addition of the amine to the acidic solution. When addition was complete a heating mantle was installed and the solution refluxed for one hour. At the end of this time the dropping funnel was charged with formaldehyde (85 g of a 37% aqueous solution) which was added dropwise over a two hour period with continued heating to maintain reflux during the addition. After all the formaldehyde was added, the reaction mixture was stirred under reflux for an additional two hours, then allowed to cool. Hydroxyethylethylenediaminetrimethylenephosphonic acid (HEEDTMP) was isolated from the reaction mixture.

EXAMPLE 6

A quantity of 30 to 40 milligrams of HEEDTMP was weighed into a vial and dissolved using 0.75 ml of distilled water. To this, 0.25 ml of Sm-153 (~10 mCi) in dilute HCl was added. The pH of the resulting solution was then adjusted to 10 by addition of NaOH. The solution was then heated between 60°-70° C. for 30 minutes in a water bath. The pH of the solution was then adjusted to 7-8 by addition of HCl. This composition was then injected into rats and the biolocalization of Sm-153 was determined.

EXAMPLE 7

Into a suitable reaction vessel equipped with a thermometer, magnetic stirring bar, dropping funnel, and an atmosphere of nitrogen were charged phosphorous acid (57.7 g) and degassed water (50 ml). Dissolution of the phosphorous acid was achieved by stirring and concentrated hydrochloric acid (50 ml) was added. The dropping funnel was charged with tris(2-aminoethyl)amine (13.7 g) and adjusted to allow dropwise addition of the amine to the acidic solution. When addition was complete a heating mantle was installed and the solution refluxed for one hour. At the end of this time the dropping funnel was charged with formaldehyde (51 g of a 37% aqueous solution) which was added dropwise over a two hour period with continued heating to maintain reflux during the addition. After all the formaldehyde was added, the reaction mixture was stirred under reflux for an additional two hours, then allowed to cool. Tris(2-aminoethyl)amine-hexamethylenephosphonic acid (TTHMP) was isolated.

EXAMPLE 8

A quantity of 48 to 53 milligrams of TTHMP was weighed into a vial and dissolved using 0.75 ml of distilled water. To this solution, 0.25 ml of Sm-153 (~10 mCi) in dilute HCl was added. The pH of the resulting solution was adjusted to 10 by addition of NaOH. The solution was then heated between 60°-70° C. for 30 minutes in a water bath. The pH of the solution was then adjusted to 7-8 by addition of HCl. This composition was then injected into rats and the biolocalization of Sm-153 was determined.

The data obtained with respect to the two hour biolocalization of Sm-153 in rats for the compositions of Examples 2, 4, 6 and 8 is shown in Table I. The numbers given for each Example represent the percentage of the administered dose which localized in the indicated tissue. The ratios of radioactivity observed in bone relative to blood and muscle were calculated based on the percent dose per gram in the bone and in the blood and muscle. These are also shown in Table I. Whenever in the following examples and tables the ratios of radioactivity found in bone to that found in non-osseous tissue is given, the calculation was made as indicated above on a percent dose per gram basis.

TABLE I

| % Dose in | Example Nos. | | | |
|---|---|---|---|---|
| | 2 | 4 | 6 | 8 |
| Skeleton | 58 | 30 | 57 | 28 |
| Blood | 0.032 | 0.16 | 0.035 | 0.25 |
| Liver | 0.25 | 0.27 | 0.45 | 0.18 |
| Urine | 49 | 74 | 50 | 65 |
| Bone/Blood | 1800 | 224 | 1300 | 80 |
| Bone/Muscle | 1500 | 220 | 1300 | 410 |

The numbers given in Table 1 represent the average of the results of five rats tested per example.

EXAMPLE 9

A quantity of 35 to 45 milligrams of EDTMP was weighed into a vial and dissolved using 0.75 ml of distilled water. To this solution, 0.25 ml of Yb-175 in dilute HCl was added. The pH of the resulting solution was adjusted to 10 by addition of NaOH. The solution was then heated between 60°-70° C. for 30 minutes in a water bath. The pH of the solution was then adjusted to 7-8 by addition of HCl.

EXAMPLE 10

A quantity of 55 to 60 milligrams of DTPMP was weighed into a vial and dissolved using 0.75 ml of distilled water. To this solution, 0.25 ml of Yb-175 in dilute HCl was added. The pH of the resulting solution was adjusted to 10 by addition of NaOH. The solution was then heated between 60°-70° C. for 30 minutes in a water bath. The pH of the solution was then adjusted to 7-8 by addition of HCl.

EXAMPLE 11

A quantity of 50 to 55 milligrams of HEEDTMP was weighed into a vial and dissolved with 0.75 ml of distilled water. To this solution, 0.25 ml of Yb-175 in dilute HCl was added. The pH of the resulting solution was adjusted to 10 by addition of NaOH. The solution was then heated between 60°-70° C. for 30 minutes in a water bath. The pH of the solution was then adjusted to 7-8 by addition of HCl.

EXAMPLE 12

Into a suitable reaction vessel equipped with a thermometer, magnetic stirring bar, dropping funnel, and an atmosphere of nitrogen were charged phosphorous acid (94.5 g) and degassed water (100 ml). Dissolution of the phosphorous acid was achieved by stirring and concentrated hydrochloric acid (112 ml) was added. The dropping funnel was charged with ammonium chloride (17.2 g in an aqueous solution) and adjusted to allow dropwise addition of the ammonium chloride to the acidic solution. When addition was complete a heating mantle was installed and the solution refluxed for one hour. At the end of this time the dropping funnel was charged with formaldehyde (85 g of a 37% aqueous solution) which was added dropwise over a two hour period with continued heating to maintain reflux during the addition. After all the formaldehyde was added, the reaction mixture was stirred under reflux for an additional two hours, then allowed to cool, yielding nitrilotrimethylenephosphonic acid (NTMP).

EXAMPLE 13

A quantity of 50 to 55 milligrams of NTMP was weighed into a vial and dissolved with 0.75 ml of distilled water. To this solution, 0.25 ml of Yb-175 in dilute HCl was added. The pH of the resulting solution was then adjusted to 10 by addition of NaOH. The solution was then heated between 60°-70° C. for 30 minutes. The pH of the solution was then adjusted to 7-8 by addition of HCl.

The compositions of Examples 9, 10, 11 and 13 were each injected into rats and the two hour biolocalization of Yb-175 for each of these compositions was determined: the data obtained is shown in Table II.

TABLE II

| % Dose in | Example Nos. | | | |
|---|---|---|---|---|
| | 9 | 10 | 11 | 13 |
| Skeleton | 50 | 25 | 56 | 63 |
| Blood | 0.074 | 0.116 | 0.231 | 0.204 |
| Liver | 0.138 | 0.112 | 0.214 | 0.236 |
| Bone/Blood | 562 | 179 | 190 | 256 |
| Bone/Muscle | 619 | 366 | 572 | 876 |

The numbers given in Table II represent the average of the results of five rats tested per example.

EXAMPLE 14

A quantity of 50 to 55 milligrams of EDTMP was weighed into a vial and dissolved with 0.75 ml of distilled water. To this solution, 0.25 ml of Lu-177 in dilute HCl was added. The pH of the resulting solution was adjusted to 10 by addition of NaOH. The solution was then heated between 60°-70° C. for 30 minutes. The pH of the solution was then adjusted to 7-8 by addition of HCl.

EXAMPLE 15

A quantity of 55 to 60 milligrams of HEEDTMP was weighed into a vial and dissolved with 0.75 ml of distilled water. To this, 0.25 ml of Lu-177 in dilute HCl was added. The pH of the resulting solution was adjusted to 10 by addition of NaOH. The solution was then heated between 60°-70° C. for 30 minutes. The pH of the solution was then adjusted to 7-8 by addition of HCl.

EXAMPLE 16

A quantity of 25 to 35 milligrams of EDTMP was weighed into a vial and dissolved with 0.75 ml of distilled water. To this solution 0.25 ml of Ho-166 in dilute HCl was added. The pH of the resulting solution was adjusted to between 7-8.

The compositions of Examples 14, 15, and 16 were each injected into rats and the two hour biolocalization of the radionuclide for each of the compositions was determined: the data obtained is shown in Table III.

TABLE III

| % Dose in | Example Nos. | | |
|---|---|---|---|
| | 14 | 15 | 16 |
| Skeleton | 51 | 58 | 48 |
| Blood | 0.10 | 0.17 | 0.03 |
| Liver | 0.48 | 1.9 | 0.05 |
| Kidneys | 0.28 | 0.30 | 0.26 |
| Muscle | 0.44 | 0.56 | 0.10 |
| Bone/Blood | 500 | 370 | 1114 |
| Bone/Muscle | 1380 | 570 | 2292 |

The numbers given in Table III for Examples 14, 15, and 16 represent the average of the results of five, five, and three rats, respectively.

EXAMPLE 17

Bis(aminoethyl)piperazinetetramethylenephosphonic acid (AEPTMP) was prepared from bis(aminoethyl)piperazine in a manner similar to Example 1. AEPTMP was complexed with Sm-153 and the biolocalization of the Sm-153 determined in rats.

EXAMPLE 18

1-Carboxyethylenediaminetetramethylenephosphonic acid (CEDTMP) was prepared from 1-carboxyethylenediamine in a manner similar to Example 1. CEDTMP was complexed with Sm-153 and the biolocalization of the SM-153 determined in rats.

The data obtained with respect to the two hour biolocalization of Sm-153 in rats for the compositions of Examples 17 and 18 is shown in Table IV.

TABLE IV

| % Dose in | Example Nos. | |
|---|---|---|
| | 17 | 18 |
| Skeleton | 48 | 57 |
| Blood | 0.24 | 0.27 |
| Liver | 2.1 | 2.2 |
| Muscle | 0.65 | 1.4 |
| Bone/Blood | 150 | 217 |
| Bone/Muscle | 364 | 376 |

The numbers given in Table IV for Examples 17 and 18 represent the average of the results of four and two rats, respectively.

EXAMPLE 19

A quantity of 48 to 53 milligrams of EDTMP was weighed into a vial and dissolved with 0.75 ml of distilled water. To this solution, 0.25 ml of Gd-159 in dilute HCl was added. The pH of the resulting solution was adjusted to 10 by addition of NaOH. The solution was then heated between 60°-70° C. in a water bath. The pH of the solution was then adjusted to 7–8 by addition of HCl.

EXAMPLE 20

A quantity of 55 to 60 milligrams of HEEDTMP was weighed into a vial and dissolved with 0.75 ml of distilled water. To this solution, 0.25 ml of Gd-159 in dilute HCl was added. The pH of the resulting solution was adjusted to 10 by addition of NaOH. The solution was then heated between 60°–70° C. in a water bath. The pH of the solution was then adjusted to 7–8 by addition of HCl.

The data obtained with respect to the two hour biolocalization of Gd-159 in rats for the compositions of Examples 19 and 20 is shown in Table V.

TABLE V

| % Dose in | Example No. 19 | Example No. 20 |
|---|---|---|
| Skeleton | 57 | 60 |
| Blood | 0.15 | 0.14 |
| Liver | 0.25 | 0.57 |
| Kidneys | 0.33 | 0.58 |
| Muscle | 0.56 | 0.76 |
| Bone/Blood | 305 | 335 |
| Bone/Muscle | 577 | 548 |

The numbers given in Table V represent the average of the results of five rates per example.

EXAMPLE 21

A series of rats was injected with compositions containing Sm-153 EDTMP (compositions prepared as in Example 2) and sacrified in groups of five at various intervals. The biolocalization data, along with the calculated bone to blood and bone to muscle ratios, is summarized in Table VI. The data shows rapid uptake of the radioactivity in bone and rapid blood clearance, as well as no significant clearance of the radioactivity from the skeletal system throughout the course of the experiment.

TABLE VI

| | Average Percent of Injected Dose at: | | | | | | | |
|---|---|---|---|---|---|---|---|---|
| Organ | 15 Min. | 30 Min. | 1 Hour | 2 Hours | 5 Hours | 24 Hours | 48 Hours | 72 Hours |
| Skeleton | 48 | 53 | 58 | 58 | 59 | 52 | 60 | 57 |
| Blood | 5.852 | 2.304 | .532 | .032 | .008 | .007 | .006 | .006 |
| Liver | .959 | .526 | .322 | .252 | .370 | .349 | .458 | .492 |
| Kidneys | 1.745 | .805 | .466 | .254 | .364 | .250 | .286 | .216 |
| Urine | 28 | 42 | 47 | 49 | 46 | 55 | 50 | 53 |
| Bone/Muscle | 30 | 70 | 300 | 1500 | 3600 | 2400 | 2800 | 3400 |
| Bone/Blood | 7 | 20 | 120 | 1800 | 4200 | 6700 | 8200 | 7800 |

EXAMPLE 22

Compositions containing Sm-153-EDTMP (compositions prepared as in Example 2) were also tested in rabbits. Results of three hour biolocalization testing (averaged for 5 rabbits) are summarized in Table VII.

TABLE VII

| % Dose in | |
|---|---|
| Skeleton | 66 |
| Blood | 0.12 |
| Liver | 0.95 |
| Urine | 34 |
| Bone Marrow | 0.15 |
| Bone/Blood | 900 |
| Bone/Muscle | 1200 |

EXAMPLE 23

An English Setter with a tumor in his pelvis was injected with approximately 19 mCi of a composition containing Sm-153-EDTMP. After 2 hours, the dog was imaged using a scintillation camera. The scintillation scan showed high uptake of radioactivity in the area of the tumor and looked very similar to an earlier scan performed using Tc-99m-MDP. The lesion to normal bone ratio for Sm-153 was very similar to that for Tc-99m. The scintillation scan of the dog five days after treatment was similar to the scintillation scan obtained two hours post injection. Seven days after the treatment the dog appeared to be in less pain as evidenced by an increase in its mobility.

EXAMPLE 24

An Irish Setter with a tumor in the femur was injected with a composition containing Sm-153-EDTMP. The leg was amputated and samples of the tumor and normal bone were analyzed for Sm-153. The amount of Sm-153 in the tumor on a per gram basis was 15–20 times that in non-lesionous bone from the same leg.

EXAMPLE 25

An Irish setter with undifferentiated sarcoma metastatic to bone was treated with 16 mCi (0.57 mCi/kg) of a composition containing Sm-153-EDTMP. Scintillation scans showed high uptake of Sm-153 in the area of the lesion and were very similar to scans obtained earlier using Tc-99m-MDP. Seven days after treatment the dog appeared to be in less pain as evidenced by an increase in mobility and a decrease in lameness. After approximately 3 months, when signs of lameness began to reappear, the dog was given a second treatment of 15 mCi (0.49 mCi/kg), of a composition containing Sm-153-EDTMP. Once again, after seven days the dog showed a general increase in mobility and decrease in lameness. X-rays taken five months after the second treatment demonstrated significant regression of bone lesions. Eight months after the second treatment the dog had no recurrence of lameness, had gained weight and appeared healthy. Nine months after the second treatment the dog died of kidney failure. Total necropsy found no evidence of cancer.

EXAMPLE 26

A series of normal beagles was treated with various dose levels of a composition containing Sm-153-EDTMP. White blood cell and platelet counts were measured weekly to check for signs of bone marrow supression. Dogs given a dose of 1.0 mCi Sm-153 per kilogram of body weight showed a slight decrease in both platelets and white blood cells 2–3 weeks after administration of the composition. White cells and platelets, returned to normal levels 4–5 weeks after administration.

Dogs given a dose of 0.5 mCi of Sm-153 per kilogram of body weight showed a smaller decrease in the levels of platelets and white blood cells. The few animals that did fall below normal platelet and white blood cell levels 2–3 weeks after administration of the Sm-153-EDTMP composition, returned to normal levels 4–5 weeks after administration.

EXAMPLE 27

Sterile pyrogen-free vials were prepared to contain 210 mg of EDTMP and 140 mg NaOH by freeze-drying a solution containing appropriate amounts of EDTMP and NaOH. The vials were sealed under vacuum. To prepare one of the compositions of the invention, 6 ml of a solution containing Sm-153 (approximately $3 \times 10^{-4}$ M in Sm) in 0.1 M HCl was injected into the sealed vial through a septum. The resulting solution had a pH of 7–8.

Five humans with metastatic bone cancer (three with lung cancer and two with prostate cancer as the primary site) were injected with a composition containing 2 mCi of Sm-153-EDTMP. Blood samples were taken intermittently to determine the fraction of the Sm-153 remaining in the blood. The results shown in Table VIII show that the radioactivity cleared very rapidly from the blood. There was no significant concentration of radioactivity in red cells since all of the measured activity was in the plasma fraction.

Urine was collected and counted to determine the percentage of the radioactivity excreted as a function of time after injection. The results in Table IX show that the fraction of radioactivity which cleared into the urine cleared rapidly.

Scintigraphic images were obtained two hours post injection and were used for comparison with images previously obtained using Tc-99m-HDP (hydroxymethylenediphosphonate), a commercially available diagnostic bone imaging agent. These images indicated that the Sm-153 localized in skeletal tissue with no significant uptake and retention in non-osseous tissues indicating a rapid and efficient clearing of Sm-153 from the blood and all other non-osseous tissues.

In addition, there is no observable retention of radioactivity in the kidneys, even in the two hour post injection images. This contrasts with the two hour images with Tc-99m HDP in which the kidneys were visualized.

Vital signs were measured at several post injection times and were not significantly different than pre-injection values. No significant changes in blood profiles (e.g., white blood cell count, red blood cell count or platelet count) or in serum chemistry profiles were observed in post-injection blood samples as compared to the pre-injection sample values.

Qualitative comparisons of images obtained using compositions containing Tc-99m-HDP and compositions containing Sm-153-EDTMP demonstrate that all cancerous lesions observable with Tc-99m-HDP are seen equally well with Sm-153-EDTMP.

The uptake observed for each radionuclide in selected lesions compared to its uptake in normal bone was determined using digitized images. The quantitative comparisons of the radioactivity in lesions and in normal bone show that compositions containing Sm-153-EDTMP and compositions containing Tc-99m-HDP result in localization of radioactivity in the lesions to a similar extent.

The results obtained in the testing with humans show an overall biolocalization profile, as well as a Sm-153 concentration in cancerous lesions which was high, selective and similar to that observed in dogs.

TABLE VIII

Blood Clearance in Humans with Metastatic Bone Disease

| Patient No. | Percent Injected Dose Remaining in Whole Blood | | | | | | |
|---|---|---|---|---|---|---|---|
| | 5 min. | 15 min. | 30 min. | 60 min. | 120 min. | 180 min. | 240 min. |
| 1 | 36.34 | 27.62 | 18.69 | 11.63 | 6.23 | 3.74 | 2.28 |
| 2 | 27.98 | 17.61 | 15.18 | 9.07 | 5.51 | 3.75 | 2.68 |
| 3 | 22.25 | 14.25 | 9.93 | 6.04 | 3.41 | 2.03 | 1.31 |
| 4 | 22.33 | 19.09 | 16.64 | 10.08 | 5.35 | 3.55 | 1.86 |
| 5 | 49.24 | 25.91 | 18.41 | 10.84 | 5.35 | 3.32 | 2.29 |
| Average | 31.63 | 20.90 | 15.77 | 9.53 | 5.17 | 3.28 | 2.08 |

TABLE IX

Percent Excretion in Urine in Humans with Metastatic Bone Disease

| Patient No. | 1 Hr. | 2 Hr. | 4 Hr. | 4–8 Hr. | 8–12 Hr. | 12–24 Hr. | 24 Hr Total |
|---|---|---|---|---|---|---|---|
| 1 | 26.09 | 10.71 | 8.84 | 11.69 | 1.67 | 1.63 | 60.63 |
| 2 | 32.28 | 2.84 | 19.30 | 12.03 | 2.17 | 1.29 | 69.91 |
| 3 | 25.55 | 4.81 | 8.29 | 3.18 | 1.72 | 0.87 | 44.42 |
| 4 | 11.37 | 9.42 | 9.87 | 12.94 | 2.24 | 0.85 | 46.69 |
| 5 | 35.36 | 7.96 | 8.47 | 5.29 | 0.98 | 0.73 | 58.79 |
| Average | 26.13 | 7.15 | 10.95 | 9.02 | 1.76 | 1.07 | 56.09 |

COMPARATIVE EXAMPLES

In a method similar to that previously used, compositions were prepared containing complexes of Sm-153 with several commercially available phosphonic acids which do not contain the alkylene linkage between the nitrogen and the phosphorus atoms.

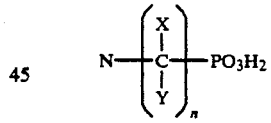

The two hour bilocalization of Sm-153 in rats for these compositions was determined as previously described. The results are given in Table A. The ligands used include methylendiphosphonic acid (MDP) and hydroxyethylidinediphosphonic acid (HEDP) which contain a P—$CH_2$—$PO_3H_2$ and a P—$C(CH_3)(OH)$—$PO_3H_2$ linkage, respectively; pyrophosphate (PYP) which contains a P—O—$PO_3H_2$ linkage: and imidodiphosphate (IDP) which contains a N—$PO_3H_2$ linkage. Metal complexes of these ligands are known skeletal agents. For example, Tc complexes of MDP, HEDP, and PYP have been used commercially as diagnostic bone agents. However, these ligands were inadequate for selectively delivering Sm-153 to the skeletal system as exemplified by the low bone to soft tissue ratios. In most cases, a large fraction of the radioactivity was found in the liver.

Table A shows the biolocalization of Sm-153 in rats two hours after injection and the results represent the percent of injected dose in tissue.

TABLE A

| % Dose In | Sm-153 MDP | Sm-153 HEDP | Sm-153 PYP | Sm-153 IDP |
|---|---|---|---|---|
| Bone | 2 | 21 | 2 | 0.6 |
| Liver | 85 | 3.5 | 73 | 36 |
| Blood | 0.23 | 13 | 0.23 | 0.04 |
| Bone/Blood | 9 | 1 | 7 | 11 |
| Bone/Muscle | 7 | 11 | 15 | 8 |

The numbers given in Table A for Sm-153-MDP, Sm-153-HEDP, Sm-153-PYP and Sm-153-IDP represent the average of the results of five, five, three and three rats, respectively.

We claim:

1. A therapeutically effective composition comprising an aminophosphonic acid which is ethylenediaminetetramethylenephosphonic acid or a physiologically acceptable salt thereof and at least one radionuclide selected from Gd-159, Ho-166, Lu-177 and Yb-175.

2. The composition of claim 1 wherein the radionuclide is Gd-159.

3. The composition of claim 1 wherein the radionuclide is Yb-175.

4. The composition of claim 1 wherein the radionuclide is Lu-177.

5. The composition of claim 1 wherein the radionuclide is Ho-166.

6. A therapeutically effective composition comprising an aminophosphonic acid which is hydroxyethylethylenediaminetrimethylenephosphonic acid or a physiologically acceptable salt thereof and at least one radionuclide selected from Gd-159, Ho-166, Lu-177 and Yb-175.

7. The composition of claim 6 wherein the radionuclide is Gd-159.

8. The composition of claim 6 wherein the radionuclide is Yb-175.

9. The composition of claim 6 wherein the radionuclide is Lu-177.

10. The composition of claim 6 wherein the radionuclide is Ho-166.

11. A therapeutically effective composition comprising an aminophosphonic acid which is diethylenetriaminepentamethylenephosphonic acid or a physiologically acceptable salt thereof and the radionuclide Yb-175.

12. A therapeutically effective composition comprising an aminophosphonic acid which is nitrilotrimethylenephosphonic acid or a physiologically acceptable salt thereof and the radionuclide Yb-175.

13. A therapeutically effective composition comprising Yb-175 and at least one of nitrilotrimethylenephosphonic acid, ethylenediaminetetramethylenephosphonic acid, hydroxyethylethylenediaminetrimethylenephosphonic acid, and diethylenetriaminepentamethylenephosphonic acid, or a physiologically acceptable salt thereof.

14. A therapeutically effective composition comprising Ho-166 and at least one of ethylenediaminetetramethylenephosphonic acid and hydroxyethylethylenediaminetrimethylenephosphonic acid or a physiologically acceptable salt thereof.

15. A therapeutically effective composition comprising Lu-177 and at least one of ethylenediaminetetramethylenephosphonic acid and hydroxyethylethylenediaminetrimethylenephosphonic acid or a physiologically acceptable salt thereof.

16. A therapeutically effective composition comprising Gd-159 and at least one of ethylenediaminetetramethylenephosphonic acid and hydroxyethylethylenediaminetrimethylenephosphonic acid or a physiologically acceptable salt thereof.

17. A method for the therapeutic treatment of an animal having one or more calcific tumors which comprises administering to said animal a therapeutically effective amount of at least one composition comprising an aminophosphonic acid which is ethylenediaminetetramethylenephosphonic acid or a physiologically acceptable salt thereof and at least one radionuclide selected from Gd-159, Ho-166, Lu-177 and Yb-175.

18. The method of claim 17 wherein the radionuclide is Gd-159.

19. The method of claim 17 wherein the radionuclide is Yb-175.

20. The method of claim 17 wherein the radionuclide is Lu-177.

21. The method of claim 17 wherein the radionuclide is Ho-166.

22. A method for the therapeutic treatment of an animal having one or more calcific tumors which comprises administering to said animal a therapeutically effective amount of at least one composition comprising an aminophosphonic acid which is diethylenetriaminepentamethylenephosphonic acid or a physiologically acceptable salt thereof and the radionuclide Yb-175.

23. A method for the therapeutic treatment of an animal having one or more calcific tumors which comprises administering to said animal a therapeutically effective amount of at least one composition comprising an aminophosphonic acid which is nitrilotrimethylenephosphonic acid or a physiologically acceptable salt thereof and the radionuclide is Yb-175.

24. A method for the therapeutic treatment of an animal having one or more calcific tumors which comprises administering to said animal a therapeutically effective amount of a composition comprising Yb-175 and at least one of nitrilotrimethylenephosphonic acid-, ethylenediaminetetramethylenephosphonic acid, hydroxyethylethylenediaminetrimethylenephosphonic acid, and diethylenetriaminepentamethylenephosphonic acid, or a physiologically acceptable salt thereof.

25. A method for the therapeutic treatment of an animal having one or more calcific tumors which comprises administering to said animal a therapeutically effective amount of a composition comprising Ho-166 and at least one of ethylenediaminetetramethylenephosphonic acid and hydroxyethylethylenediaminetrimethylenephosphonic acid or a physiologically acceptable salt thereof.

26. A method for the therapeutic treatment of an animal having one or more calcific tumors which comprises administering to said animal a therapeutically effective amount of a composition comprising Lu-177 and at least one of ethylenediaminetetramethylenephosphonic acid and hydroxyethylethylenediaminetrimethylenephosphonic acid or a physiologically acceptable salt thereof.

27. A method for the therapeutic treatment of an animal having one or more calcific tumors which comprises administering to said animal a therapeutically effective amount of a composition comprising Gd-159 and at least one of ethylenediaminetetramethylenephosphonic acid and hydroxyethylethylenediaminetrimethylenephosphonic acid or a physiologically acceptable salt thereof.

28. A composition comprising 1) a complex which comprises at least one radionuclide selected from Gd-159, Ho-166, Lu-177 and Yb-175 and at least one of aminophosphonic acid, or a physiologically acceptable salt thereof, wherein the aminophosphonic acid is selected from the group consisting of ethylenediaminetetramethylenephosphonic acid, diethylenetriaminepentamethylenephosphonic acid, hydroxyethylethylenediaminetrimethylenephosphonic acid and nitrilotrimethylenephosphonic acid, and 2) at least one of the above aminophosphonic acids, or a physiologically acceptable salt thereof, in excess of that required to make the complex, and wherein the resulting composition is therapeutically effective.

29. The composition of claim 28 wherein a physiologically acceptable liquid carrier is present.

30. The composition of claim 29 wherein the physiologically acceptable liquid carrier is water and the resulting solution is adjusted to have a pH of about 7 to about 8.

31. The composition of claim 28 wherein the radionuclide is Gd-159.

32. The composition of claim 31 wherein the aminophosphonic acid is selected from the group consisting of ethylenediaminetetramethylenephosphonic acid and hydroxyethylethylenediaminetrimethylenephosphonic acid, or a physiologically acceptable salt thereof.

33. The composition of claim 28 wherein the radionuclide is Ho-166.

34. The composition of claim 33 wherein the aminophosphonic acid is selected from the group consisting of ethylenediaminetetramethylenephosphonic acid and hydroxyethylethylenediaminetrimethylenephosphonic acid, or a physiologically acceptable salt thereof.

35. The composition of claim 28 wherein the radionuclide is Lu-177.

36. The composition of claim 35 wherein the aminophosphonic acid is selected from the group consisting of ethylenediaminetetramethylenephosphonic acid and hydroxyethylethylenediaminetrimethylenephosphonic acid, or a physiologically acceptable salt thereof.

37. The composition of claim 28 wherein the radionuclide is Yb-175.

38. A sterile composition suitable for administration to a mammal comprising 1) a complex which comprises at least one radionuclide selected from Gd-159, Ho-166, Lu-177 and Yb-175 and at least one of an aminophosphonic acid, or a physiologically acceptable salt thereof, wherein the aminophosphonic acid is selected from the group consisting of ethylenediaminetetramethylenephosphonic acid, diethylenetriaminepentamethylenephosphonic acid, hydroxyethylethylenediaminetrimethylenephosphonic acid and nitrilotrimethylenephosphonic acid and nitrilotrimethylenephosphonic acid, and 2) at least one of the above aminophosphonic acids, or a physiologically acceptable salt thereof, in excess of that required to make the complex, and wherein the resulting composition is therapeutically effective and wherein the radionuclide in dosage form is present in an amount containing at least 0.02 mCi per kilogram of body weight of said mammal.

39. The composition of claim 38 wherein a physiologically acceptable liquid carrier is present.

40. The composition of claim 39 wherein the physiologically acceptable liquid carrier is water and the resulting solution is adjusted to have a pH of about 7 to about 8.

41. The composition of claim 38 wherein the radionuclide is Gd-159.

42. The composition of claim 41 wherein the aminophosphonic acid is selected from the group consisting of ethylenediaminetetramethylenephosphonic acid and hydroxyethylethylenediaminetrimethylenephosphonic acid, or a physiologically acceptable salt thereof.

43. The composition of claim 38 wherein the radionuclide is Ho-166.

44. The composition of claim 43 wherein the aminophosphonic acid is selected from the group consisting of ethylenediaminetetramethylenephosphonic acid and hydroxyethylethylenediaminetrimethylenephosphonic acid, or a physiologically acceptable salt thereof.

45. The composition of claim 38 wherein the radionuclide is Lu-177.

46. The composition of claim 45 wherein the aminophosphonic acid is selected from the group consisting of ethylenediaminetetramethylenephosphonic acid and hydroxyethylethylenediaminetrimethylenephosphonic acid, or a physiologically acceptable salt thereof.

47. The composition of claim 38 wherein the radionuclide is Yb-175.

48. A method for the therapeutic treatment of an animal having one or more calcific tumors which comprises administering to said animal a therapeutically effective amount of a composition comprising 1) a complex which comprises at least one radionuclide selected from Gd-159, Ho-166, Lu-177 and Yb-175 and at least one of an aminophosphonic acid, or a physiologically acceptable salt thereof, wherein the aminophosphonic acid is selected from the group consisting of ethylenediaminetetramethylenephosphonic acid, diethylenetriaminepentamethylenephosphonic acid, hydroxyethylethylenediaminetrimethylenephosphonic acid and nitrilotrimethylenephosphonic acid, and 2) at least one of the above aminophosphonic acids, or a physiologically acceptable salt thereof, in excess of that required to make the complex.

49. The method of claim 48 wherein the animal is a human.

50. The method of claim 48 wherein a physiologically acceptable liquid carrier is present.

51. The method of claim 50 wherein the physiologically acceptable liquid carrier is water and the resulting solution is adjusted to have a pH of about 7 to about 8.

52. A method of claim 48 wherein the complex comprises as the radionuclide Gd-159 and as the aminophosphonic acid, or a physiologically acceptable salt thereof, an aminophosphonic acid selected from the group consisting of ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

53. The method of claim 52 wherein the animal is a human.

54. The method of claim 52 wherein a physiologically acceptable liquid carrier is present.

55. The method of claim 54 wherein the physiologically acceptable liquid carrier is water and the resulting solution is adjusted to have a pH of about 7 to about 8.

56. A method of claim 48 wherein the complex comprises as the radionuclide Ho-166 and as the aminophosphonic acid, or a physiologically acceptable salt thereof, an aminophosphonic acid selected from the grouping consisting of ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

57. The method of claim 56 wherein the animal is a human.

58. The method of claim 56 wherein a physiologically acceptable liquid carrier is present.

59. The method of claim 58 wherein the physiologically acceptable liquid carrier is water and the resulting solution is adjusted to have a pH of about 7 to about 8.

60. A method of claim 48 wherein the complex comprises as the radionuclide Lu-177 and as the aminophosphonic acid, or a physiologically acceptable salt thereof, an aminophosphonic acid selected from the group consisting of ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

61. The method of claim 60 wherein the animal is a human.

62. The method of claim 60 wherein a physiologically acceptable liquid carrier is present.

63. The method of claim 62 wherein the physiologically acceptable liquid carrier is water and the resulting solution is adjusted to have a pH of about 7 to about 8.

64. A method of claim 48 wherein the complex comprises as the radionuclide Yb-175 and as the aminophosphonic acid, or a physiologically acceptable salt thereof, an aminophosphonic acid selected from the group consisting of diethylenetriaminepentamethylenephosphonic acid, nitrilotrimethylenephosphonic acid, ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

65. The method of claim 64 wherein the animal is a human.

66. The method of claim 64 wherein a physiologically acceptable liquid carrier is present.

67. The method of claim 66 wherein the physiologically acceptable liquid carrier is water and the resulting solution is adjusted to have a pH of about 7 to about 8.

68. A method for the therapeutic treatment of an animal having bone pain which comprises administering to said animal a therapeutically effective amount of a composition comprising 1) a complex which comprises at least one radionuclide selected from Gd-159, Ho-166, Lu-17 and Yb-175 and at least one of an aminophosphonic acid, or a physiologically acceptable salt thereof, wherein the aminophosphonic acid is selected from the group consisting of ethylenediaminetetramethylenephosphonic acid, diethylenetriaminepentamethylenephosphonic acid, hydroxyethylethylenediaminetrimethylenephosphonic acid and nitrilotrimethylenephosphonic acid, and 2) at least one of the above aminophosphonic acids, or a physiologically acceptable salt thereof, in excess of that required to make the complex.

69. The method of claim 68 wherein the animal is a human.

70. The method of claim 68 wherein a physiologically acceptable liquid carrier is present.

71. The method of claim 70 wherein the physiologically acceptable liquid carrier is water and the resulting solution is adjusted to have a pH of about 7 to about 8.

72. A method of claim 68 wherein the complex comprises as the radionuclide Gd-159 and as the aminophosphonic acid, or a physiologically acceptable salt thereof, an aminophosphonic acid selected from the group consisting of ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

73. The method of claim 72 wherein the animal is a human.

74. The method of claim 72 wherein a physiologically acceptable liquid carrier is present.

75. The method of claim 74 wherein the physiologically acceptable liquid carrier is water and the resulting solution is adjusted to have a pH of about 7 to about 8.

76. A method of claim 68 wherein the complex comprises as the radionuclide Ho-166 and as the aminophosphonic acid, or a physiologically acceptable salt thereof, an aminophosphonic acid selected from the group consisting of ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

77. The method of claim 76 wherein the animal is a human.

78. The method of claim 76 wherein a physiologically acceptable liquid carrier is present.

79. The method of claim 78 wherein the physiologically acceptable liquid carrier is water and the resulting solution is adjusted to have a pH of about 7 to about 8.

80. A method of claim 68 wherein the complex comprises as the radionuclide Lu-177 and as the aminophosphonic acid, or a physiologically acceptable salt thereof, an aminophosphonic acid selected from the group consisting of ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

81. The method of claim 81 wherein the animal is a human.

82. The method of claim 81 wherein a physiologically acceptable liquid carrier is present.

83. The method of claim 82 wherein the physiologically acceptable liquid carrier is water and the resulting solution is adjusted to have a pH of about 7 to about 8.

84. A method of claim 68 wherein the complex comprises as the radionuclide Yb-175 and as the aminophosphonic acid, or a physiologically acceptable salt thereof, an aminophosphonic acid selected from the group consisting of diethylenetriaminepentamethylenephosphonic acid, nitrilotrimethylenephosphonic acid, ethylenediaminetetramethylenephosphonic acid and hydroxyethylethylenediaminetrimethylenephosphonic acid and 2) at least one of the above aminophosphonic acids, or a physiologically acceptable salt thereof, in excess of that required to make the complex.

85. The method of claim 84 wherein the animal is a human.

86. The method of claim 84 wherein a physiologically acceptable liquid carrier is present.

87. The method of claim 86 wherein the physiologically acceptable liquid carrier is water and the resulting solution is adjusted to have a pH of about 7 to about 8.

* * * * *

UNITED STATES PATENT AND TRADEMARK OFFICE
CERTIFICATE OF CORRECTION

PATENT NO. : 5,066,478
DATED : November 19, 1991
INVENTOR(S) : Jaime Simon, et al It is certified that error appears in the above-indentified patent and that said Letters Patent is hereby corrected as shown below:

Column 19, lines 59 and 60, delete "and nitrilotrimethylenephosphonic acid".

Column 21, line 58, "Lu-17" should correctly appear as -- Lu-177 --.

Column 22, line 53, "claim 81 wherein" should correctly appear as -- claim 80 wherein --.

Column 22, line 55, "claim 81 wherein" should correctly appear as -- claim 80 wherein --.

Signed and Sealed this

Eighth Day of February, 1994

Attest:

BRUCE LEHMAN

Attesting Officer

Commissioner of Patents and Trademarks